United States Patent [19]

Mavrovic

[11] 4,088,684
[45] May 9, 1978

[54] UREA REACTOR EFFLUENT SOLUTION RECYCLE IN UREA SYNTHESIS

[76] Inventor: Ivo Mavrovic, 530 E. 72nd St., New York, N.Y. 10021

[21] Appl. No.: 710,318

[22] Filed: Jul. 30, 1976

[51] Int. Cl.$^2$ .......................................... C07C 126/02
[52] U.S. Cl. .................................................. 260/555 A
[58] Field of Search .................................. 260/555 A

[56] References Cited

U.S. PATENT DOCUMENTS

| 3,470,247 | 9/1969 | Guadalupi | 260/555 A |
| 3,573,173 | 3/1971 | Otsuka et al. | 260/555 A |
| 3,579,636 | 5/1971 | Mavrovic | 260/555 A |
| 3,759,992 | 9/1973 | Mavrovic | 260/555 A |
| 3,808,271 | 4/1974 | Mavrovic | 260/555 A |
| 3,886,210 | 5/1971 | Mavrovic | 260/555 A |

*Primary Examiner*—Edward J. Meros

*Attorney, Agent, or Firm*—Flynn & Frishauf

[57] ABSTRACT

Urea synthesis process with liquid carbamate recycle, in which the reactor effluent is divided into major and minor streams. The major stream is reduced in pressure and subjected to heating and substantial carbamate decomposition to ammonia and carbon dioxide decomposer off gas, either directly or after preliminary ammonia separation. The minor stream is reduced in pressure and is contacted with decomposer off gas and fresh make up carbon dioxide, either directly or after preliminary ammonia separation, and in indirect heat exchange with a relatively colder fluid, whereupon ammonium carbamate is formed from the mixture of the minor stream, fresh make up $CO_2$ and decomposer off gas in an aqueous solution of urea and the resulting solution is recycled to the urea synthesis reactor.

10 Claims, 1 Drawing Figure

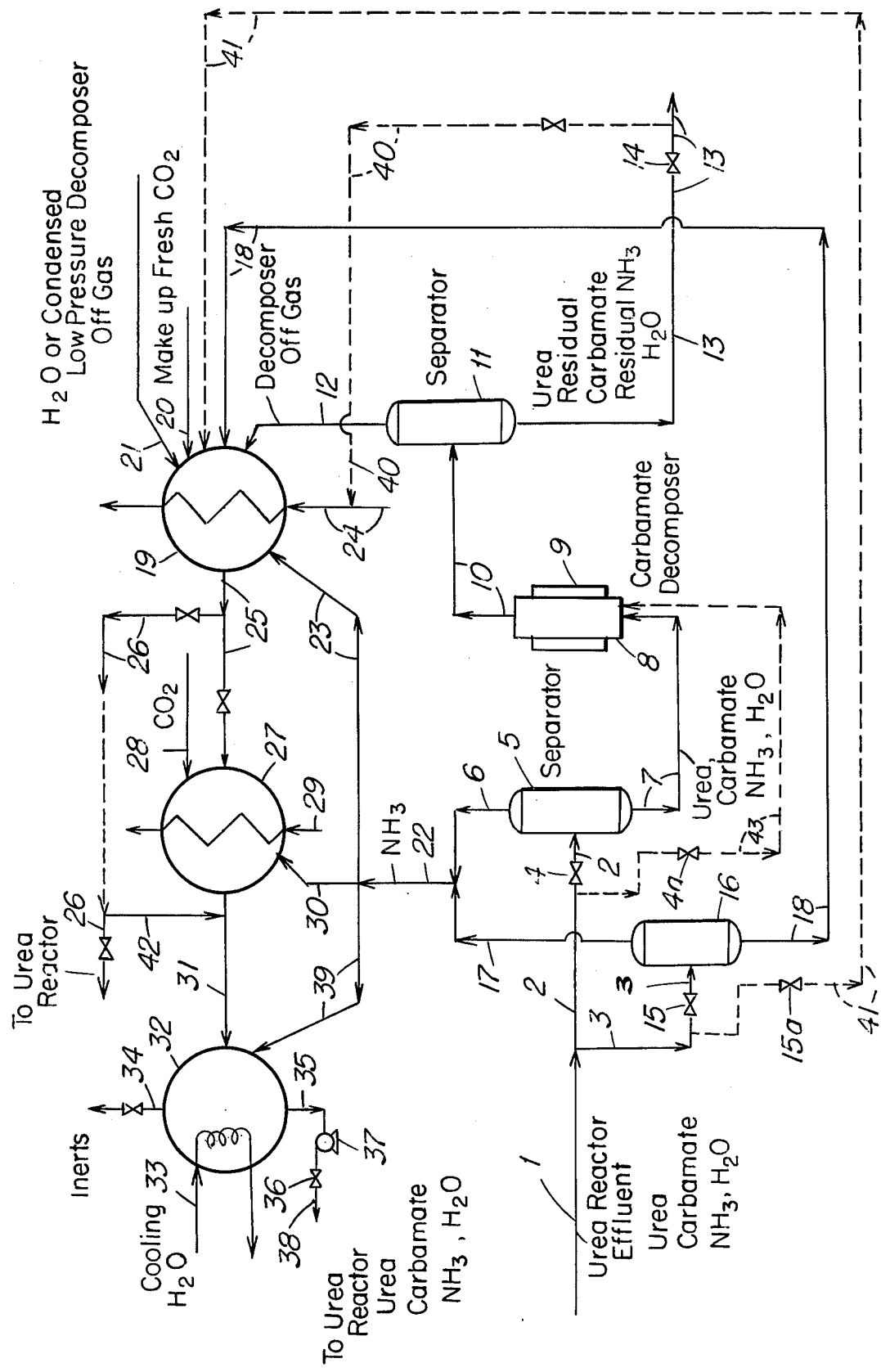

UREA REACTOR EFFLUENT SOLUTION RECYCLE IN UREA SYNTHESIS

FIELD OF INVENTION

This application has to do with the synthesis of urea from ammonia and carbon dioxide.

BACKGROUND OF INVENTION

Urea is obtained commercially by reaction of $NH_3$ and $CO_2$ in a reactor at elevated temperature and pressure. At urea synthesis conditions, $NH_3$ and $CO_2$ instantaneously and completely react stoichiometrically to form ammonium carbamate. The latter is partially converted to urea and water within 20–30 minutes of residence time in the reactor. Excess $NH_3$ above this stoichiometric ratio is used in the reactor, in an usual $NH_3$ to $CO_2$ overall mole ratio from 3/1 to 6/1, for the purpose of increasing the conversion of carbamate to urea. The urea synthesis reactor effluent containing urea, water, excess free $NH_3$ and unconverted ammonium carbamate is usually let down in pressure and heated at about 200–300 psig in a carbamate decomposer for the purpose of decomposing the unconverted ammonium carbamate to $NH_3$ and $CO_2$ gases and to boil off excess ammonia. The $NH_3$ and $CO_2$ decomposer off gas with water vapor thus recovered is absorbed in water to form an aqueous ammoniacal solution of ammonium carbamate and is recycled back into the urea reactor for total recovery.

In my U.S. Pat. Nos. 3,759,992 and 3,808,271, I have described improved processes wherein a first aqueous solution containing ammonium carbamate, ammonia, urea and water, as one formed in a urea reactor, is split into a minor portion (A) and a major portion (B). The major portion (B) is heated in an ammonium carbamate decomposer. In the decomposer, ammonium carbamate is decomposed to $NH_3$ and $CO_2$ gases, and at least part of the excess $NH_3$ and water are vaporized. A resulting gas phase (C) is expelled from a resulting liquid phase (D); phase (D) contains residual ammonium carbamate and $NH_3$ dissolved in a second aqueous urea solution. Gaseous phase (C) is then contacted countercurrently with said cooled minor portion (A), for the purpose of reducing the water vapor content of gaseous phase (C). Gaseous phase (C), thus reduced in water vapor, is contacted with fresh make up $CO_2$ and urea other than that present in the reactor effluent, with generation of heat of reaction. Such heat of reaction is transferred indirectly either to cooling water or to a relatively colder process fluid for heat recovery.

STATEMENT OF INVENTION

In accordance with my present invention, I have now discovered that substantial economies can be realized in heat exchange equipment investment and in operating utilities such as cooling water and steam requirements. In this new process sequence, a major part of the urea synthesis reactor effluent, let down in pressure and preferably separated from most of the excess ammonia in known manner, is further subjected to heating for substantial carbamate decomposition (as, for example, in U.S. Pat. Nos. 3,759,992 and 3,808,271) to produce a stream of decomposer off gas containing $CO_2$, $NH_3$ and $H_2O$. A minor part of the urea synthesis reactor effluent stream, let down in pressure and preferably separated from most of the excess ammonia contained therein, is contacted with $CO_2$—$NH_3$ decomposer off gas and fresh make up $CO_2$ in indirect heat exchange with a relatively colder fluid, and the resulting liquid mixture comprising ammonium carbamate and urea is recycled to the urea synthesis reactor.

In another embodiment of the invention, the major reactor effluent stream can be let down in pressure and directly subjected to heating for substantial carbamate decomposition without prior excess ammonia separation, and/or the minor reactor effluent stream can be let down in pressure and directly contacted with decomposer off gas and fresh make up $CO_2$, without prior removal of excess ammonia by separation, and the resulting solution recycled to the reactor.

As another embodiment, the decomposer off gas contacted with the minor part of the reactor effluent stream and with the fresh make up $CO_2$ can be supplied from another decomposer or other source extraneous to the urea synthesis section.

THE DRAWING

The FIGURE is a schematic flow diagram illustrating embodiments of the invention.

SPECIFIC EMBODIMENTS OF THE INVENTION

In the FIGURE, line 1 contains a urea reactor effluent withdrawn from a urea synthesis reactor (not shown) operated at a temperature of from about 330° F. to about 400° F. and at a pressure of from about 1500 psig to about 4000 psig, with an $NH_3$ to $CO_2$ overall molar ratio therein of from about 3:1 to about 6:1. The stream in line 1 is divided into a major stream in valved line 2 and into a minor stream in valved line 3, the amounts being described below. The major stream in line 2 is reduced in pressure through valve 4 and is passed into vessel 5 for separation of part of the excess ammonia through overhead line 6 by methods described by prior art. The remaining liquid phase containing urea, ammonium carbamate, excess ammonia and water is passed through line 7 into carbamate decomposer 8, provided with heating in its shell side 9. The heated mixture is passed from decomposer 8 through line 10 into separator 11, in which the gaseous phase is separated from the liquid phase and discharged overhead through line 12. Said gaseous phase (in 12) is formed by decomposition of carbamate into $NH_3$ and $CO_2$ and by vaporization of excess ammonia and water due to heating in decomposer 8; this gaseous phase is defined herein as "a decomposer off gas stream".

The liquid phase formed in decomposer 8 is discharged from separator 11 through line 13; this contains urea, residual ammonium carbamate, some ammonia and water. It is reduced in pressure through valve 14 and is usually fed into another low pressure decomposer (not shown) similar to decomposer 8 for further urea product degassing. Such low pressure decomposer off gas (not shown) can be either sent to an adjacent plant for ammonia recovery by neutralization, or condensed to a liquid phase and recycled to the urea synthesis section as is described further below.

The minor part of urea reactor effluent in line 3 is reduced in pressure through valve 15 and is passed into vessel 16 for separation of part of the excess ammonia gas through overhead line 17. The remaining liquid phase containing urea, ammonium carbamate, ammonia and water is passed through line 18 into one side (shell side for example) of heat exchanger 19, together with decomposer off gas in line 12. A stream of fresh make up $CO_2$ in line 20, which would be normally fed directly to the urea synthesis reactor in other processes, is admixed with the streams of lines 18 and 12, in an amount equivalent to from about 0.016 to about 0.7 times the weight of urea contained in line 13. A stream of water can be added through line 21 to said mixture of streams 12, 18 and 20; or, a stream of a liquid phase formed by condensation of low pressure decomposer off gas described before, and not shown on the drawing, can be added from line 21. Optionally, a part of stream 6 or stream 17, or part of a combination of streams 6 and 17 in line 22, can be added to the mixture of lines 12, 18, 20 and 21 in heat exchanger 19 through line 23.

Due to the evolution of heat of reaction, the temperature of the mixture in exchanger 19 is elevated to from about 230° F. to about 330° F. A relatively colder fluid (e.g., at 0°–220° F.) is passed through the other side of heat exchanger 19 (through the tube side, for example) through line 24 and heated to from about 60° F. to about 320° F. Said relatively colder fluid includes such fluids as steam condensate, cooling water, a reactor feed stream, and a stream of aqueous urea solution undergoing water evaporation and/or decomposition of carbamate to $NH_3$ and $CO_2$ gas. Heat exchanger 19 can be provided with more than one single separate coil (tube side) through which two or more separate colder fluid streams can be passed simultaneously in indirect heat exchange with the mixture in the shell side.

When total condensaion of the mixture in shell side 19 occurs, the resulting condensed liquid can be withdrawn through valved line 25 and delivered by a pump (not shown) directly to the urea synthesis reactor via valved line 26. When the fluid in line 25 still comprises unreacted gases, heat exchanger 19 can be followed by an additional heat exchanger 27 very similar to heat exchanger 19 in its operation and function. Additional $CO_2$ can be added to the shell side of exchanger 27 through line 28, in which case the amount of $CO_2$ in line 20 is reduced by a corresponding amount. A colder fluid passed through line 29 and the tube side of heat exchanger 26 can be one or more of the streams mentioned above in relation with the operation of heat exchanger 19. Optionally, a part of stream 6 or stream 17, or part of a combination of streams 6 and 17 in line 22, can be added to the shell side of heat exchanger 27 through line 30.

One or more heat exchangers similar to exchangers 19 and 27 can follow, until the major part of the heat of reaction of the mixture in the shell side of such exchangers is economically recovered and exhausted.

As an alternate embodiment, heat exchangers 19 and 27 and/or one or more others (not shown) can be connected in parallel with respect to the side of the mixture of streams 18, 20, 21 and 12 or parts thereof, if economics so dictate.

When the mixture discharged from exchanger 27 through valved line 31 still contains unreacted gas, it is passed into final condenser 32, provided with cooling water coil 33 for removal of the heat of reaction. The remaining part of separated ammonia in line 22 is passed into condenser 32 through line 39. Inerts are vented overhead and discharged into the atmosphere through valved line 34. The resulting liquid phase in condenser 32 is discharged therefrom through line 35 and delivered on level control through valve 36 to the urea synthesis reactor (not shown) by pump 37 through line 38.

As other embodiments, major stream 2 can be passed directly into the tube side of carbamate decomposer 8 through valve 4a and line 43, in which event ammonia separator 5 is not used; the low pressure liquid in line 13 can be passed through valved line 40 to line 24 for use in the operation of vessel 19; minor stream 3 can be passed directly into exchanger 19 through valve 15a and line 41, in which case separator 16 is not used. Also, exchanger 27 can be by-passed by routing the mixture in line 25 through valved line 26 and lines 42 and 31 to condenser 32.

As a further embodiment, separators 5 and 16, described below, can be combined in one single vessel into which the urea synthesis reactor effluent of line 1 is passed after reduction in pressure for ammonia separation by one of the known methods. In this case, the remaining liquid discharged from such a combined separator through its bottom line is divided in the same proportion as the stream in line 1 is divided into stream 2 and stream 3. It is important that the stream of urea solution recycled to heat exchanger 19 through line 18, or line 41, either divided directly from the urea synthesis reactor effluent stream or indirectly after reduction in pressure and ammonia separation as described above, contains from about 1% to about 49% of the amount of urea present in the urea synthesis reactor effluent solution in line 1.

Vessels 5, 16, 8, 11, 19, 27 and 32 are operated at a pressure of from about 60 psig to about 700 psig, preferably at about 300 psig. Vessels 5 and 16 are operated at a temperature of from about 200° F. to about 280° F., preferably at about 240° F. Carbamate decomposer 8 and the heated product in line 10 maintained at a temperature of from about 240° F. to about 350° F.

The shell sides of vessels 19 and 27 are operated at from about 230° F. to about 330° F. when a process fluid is passed through the corresponding tube sides 24 and 29; whereas, the shell side of condenser 32 is operated at from about 150° F. to about 260° F. with water cooling in its coil 33 for the purpose of attaining a total or partial condensation of the mixture in the shell side.

The invention is illustrated further by the following example.

A stream of urea reactor effluent in line 1 containing 34,500 parts of urea, 10,300 parts of $CO_2$, 32,900 parts of ammonia, and 19,000 parts of water, at 3100 psig pressure and 375° F., is divided into major stream 2 and minor stream 3. Major stream 2 contains 30,000 parts of urea, 8,956 parts of $CO_2$, 28,610 parts of ammonia and 16,522 parts of water. Minor stream 3 contains 4,500 parts of urea, 1,344 parts of $CO_2$, 4,290 parts of ammonia and 2,478 parts of water.

Major stream 2 is let down in pressure to 300 psig through valve 4a and is passed directly into the tube side of carbamate decomposer 8 via line 43; ammonia separator 5 is not used. Steam is supplied into steam chest 9 of decomposer 8 and the resulting mixture in line 10, heated to 320° F., is passed into separator 11. Decomposer off gas removed from separator 11 through overhead line 12 contains 7,616 parts of $CO_2$, 23,610 parts of ammonia and 3,850 parts of water vapor. The remaining liquid phase, discharged from separator 11 through bottom line 13, contains 30,000 parts of urea, 1,340 parts of $CO_2$, 5,000 parts of ammonia and 12,672 parts of water. Stream 13 is reduced in pressure through valve 14 to about 15 psig and is passed through valved line 40 and line 24 into the tube side of heat exchanger 19 for further heating and carbamate decomposition. In this case, heat exchanger 19 acts as a low pressure carbamate decomposer with respect to its function per-formed in its tube side. After decomposition of carbamate in the mixture supplied through line 24, analogously to separator 11, the low pressure decomposer mixture of line 24 of vessel 19 is introduced into a low pressure separator (not shown) for liquid gas separation. The stream of overhead low pressure decomposer off gas from the low pressure separator (not shown) can be partially or totally condensed and recycled to the shell side of heat exchanger 19 through line 21 as an aqueous solution of ammonium carbamate and ammonia.

Minor stream in line 3 is reduced in pressure to about 300 psig through valve 15a and is passed directly into the shell side of heat exchanger 19 through line 41; separator 16 is not used. 8,800 parts of fresh make up $CO_2$, taken from the total amount of 22,000 parts of make up fresh $CO_2$ required to produce urea, are delivered into the shell side of heat exchanger 19 through line 20. The remaining part of fresh make up $CO_2$ (22,000 − 8,800 = 13,200 parts) is passed directly into the urea synthesis reactor (not shown). 3,672 parts of water are passed through line 21 to maintain the concentration of carbamate in line 38 below its crystallization point. The stream in line 12 containing decomposer off gas from separator 11 is added also to the shell side of heat exchanger 19. The mixture of streams 12, 41, 20 and 21 is heated in exchanger 19 to about 290° F. adiabatically by the heat of reaction thereof, and the stream of low pressure product from lines 13 and 40 supplied through line 24, as described above, flashed to a temperature of about 230° F., is heated to about 270° F. for carbamate decomposition and urea product solution degassing. A mixture of gas and liquid is passed through line 25 and is passed directly into condenser 32 via valved line 26 and lines 42 and 31 for total condensation; heat exchanger 27 is not used. Cooling water is circulated through coil 33 to remove the heat of reaction from the shell side of heat exchanger 32. Inerts are vented to the atmosphere through valved line 34. As an alternate, by regulating the flow of cooling water through line 33, only partial condensation can be attained in condenser 32, so that substantially all the water vapor and the $CO_2$ gas in line 25 are condensed to liquid and reacted with $NH_3$ to form ammonium carbamate, whereas the major part of ammonia remains in the gaseous phase which is then vented through line 34 for further processing and recovery, not shown.

With total condensation of the mixture in condenser 32, at about 300 psig, the resulting liquid is discharged from condenser 32 through bottom line 35 at about 200° F., elevated in pressure by pump 37 and on level control from condenser 32 delivered to the urea synthesis reactor (not shown) through valve 36, and line 38. The solution in line 38 contains 17,760 parts of $CO_2$, 27,900 parts of ammonia, 10,000 parts of water and 4,500 parts of urea. The net amount of urea formed in the reactor is equal to 30,000 parts, for which a total stoichiometric amount of fresh make up $CO_2$ of 22,000 parts is required in the reactor. As explained above, part of this stoichiometric amount of $CO_2$ is delivered to the shell side of heat exchanger 19 through line 20 and the remaining part of 13,200 parts is delivered directly to the urea synthesis reactor (not shown).

The advantage of feeding a minor portion (stream 3) of reactor effluent (stream 1) directly (or indirectly after ammonia separation at reduced pressure in separator 16) through line 41 into the shell side of heat exchanger 19, instead of urea melt or aqueous urea solution other than that separated from the reactor effluent, is demonstrated by the fact that the carbamate decomposer 8 heat load (and consequent steam consumption) is decreased by the equivalent amount of heat which would be required to decompose the amount of carbamate contained in line 41, which carbamate is returned to the urea synthesis reactor (via heat exchangers 19 and 32) undecomposed. The equivalent amount of cooling water can be saved in condenser 32.

One of the benefits of this invention is that by adding urea synthesis reactor effluent and fresh make up $CO_2$ to the stream of decomposer off gas containing $NH_3$, $CO_2$ and $H_2O$, the boiling point of the resulting mixture after condensation is subtantially increased. As a consequence, the heat of reaction thereof becomes available for recovery at a much higher temperature level compared to a condensing mixture of $NH_3$—$CO_2$—$H_2O$ decomposer off gas alone without the addition of urea and fresh make up $CO_2$. As a direct consequence, a large amount of heat of reaction can be advantageously transferred to a relatively colder fluid and at a much higher temperature level, as for instance 290°–300° F. instead of 200°–230° F. Not only is more heat recovered from the condensing decomposer off gas, but the size of the heat exchanger performing the function of exchanging heat between the condensing decomposer off gas and the relatively colder process fluid can be decreased substantially because of the increase in temperature differential between the two fluids. Another benefit is that by introducing into the condensing stream of decomposer off gas a portion of the urea reactor effluent solution either directly or after excess ammonia separation thereof, instead of so introducing fresh make up urea, a considerable reduction in steam consumption is attained in the carbamate decomposer; this results because part of the ammonia and carbamate contained in the stream of urea reactor effluent solution introduced into the stream of decomposer off gas does not have to be decomposed and reabsorbed for the purpose of recycling it into the urea synthesis reactor.

Still another benefit is that by introducing into the condensing stream of decomposer off gas a portion of the fresh make up $CO_2$ required in the urea synthesis reactor to produce urea, a considerable saving in $CO_2$ gas compression power is attained due to the fact that the portion of fresh make up $CO_2$ introduced into the off gas is delivered to the urea synthesis reactor as liquid ammonium carbamate for reaction to urea, instead of being delivered to the urea synthesis reactor as gaseous $CO_2$ by power consuming compression.

I claim:
1. The process for synthesizing urea, which comprises the sequence of steps consisting essentially of
reacting ammonia and carbon dioxide in a reactor at elevated urea synthesis pressure to form an aqueous urea solution (1) containing ammonium carbamate, ammonia and water,
splitting said aqueous solution (1) into a major stream (2) thereof and a minor stream (3) thereof,
reducing the pressures of each of said major stream (2) and minor stream (3) substantially to from about 60 to about 700 pounds per square inch, heating said major stream (2) in an ammonium carbamate decomposer to a temperature above the decomposition temperature of ammonium carbamate to decompose a substantial portion of the ammonium carbamate therein to ammonia and carbon dioxide, and vaporize part of the excess ammonia and part of the water therein;

passing the resulting heated mixture from said decomposer to a separator and expelling the resulting decomposer off gas stream containing said vaporized excess ammonia and part of the water from the residual urea-containing liquid phase of said major stream (2) in said separator, and contacting said minor stream (3) directly with said resulting decomposer off gas and with fresh carbon dioxide in a heat exchanger in indirect heat exchange with a relatively colder fluid, whereby carbon dioxide contained in said decomposer off gas and fresh carbon dioxide react with ammonia to form ammonium carbamate and a product containing the same, water, urea and ammonia is obtained, and heat of formation of said ammonium carbamate is transferred to said relatively colder fluid.

2. The process of claim 1, wherein said product so formed from said decomposer off gas, from said minor stream (3) and from said fresh carbon dioxide, is recycled to said reactor.

3. The process for synthesizing urea, which comprises the sequence of steps consisting essentially of reacting ammonia and carbon dioxide in a rector at elevated urea synthesis pressure to form an aqueous urea solution (1) containing ammonium carbamate, ammonia and water, reducing the pressure of said solution (1) to from about 60 to about 700 pounds per square inch, and separating excess ammonia gas from the resulting residual liquid phase (4), splitting said residual liquid phase (4) into a major stream (5) thereof and a minor stream (6) thereof, heating said major stream (5) in an ammonium carbamate decomposer at a temperature above the decomposition temperature of ammonium carbamate to decompose a substantial portion of the ammonium carbamate therein to ammonia and carbon dioxide, and vaporize part of the excess ammonia and part of the water therein, passing the resulting heated mixture from said decomposer to a separator and expelling the resulting decomposer off gas stream containing said vaporized excess ammonia and part of the water from the residual urea-containing liquid phase of said major stream (5), and contacting said minor stream (6) directly with said resulting decomposer off gas and with fresh carbon dioxide in a heat exchanger in indirect heat exchange with a relatively colder fluid, whereby carbon dioxide contained in said decomposer off gas and fresh carbon dioxide react with ammonia to form ammonium carbamate and a product containing the same, water, urea and ammonia is obtained, and heat of formation of said ammonium carbamate is transferred to said relatively colder fluid.

4. The process of claim 3, wherein said product so formed from said decomposer off gas from said minor stream (6) and from said fresh carbon dioxide, is recycled to said reactor.

5. The process for synthesizing urea, which comprises the sequence of steps consisting essentially of reacting ammonia and carbon dioxide in a reactor at elevated urea synthesis pressure to form an aqueous urea solution (1) containing ammonium carbamate, ammonia and water, splitting said aqueous solution (1) into a major stream (2) thereof and a minor stream (3) thereof, reducing the pressure of each of streams (2) and (3) substantially to from about 60 to about 700 pounds per square inch, whereby excess ammonia gas is removed therefrom to form a resulting major stream (2) and a resulting minor stream (3), respectively, heating said resulting major stream (2) in an ammonium carbamate decomposer at a temperature above the decomposition temperature of ammonium carbamate to decompose a substantial portion of the ammonium carbamate therein to ammonia and carbon dioxide, and vaporize part of the excess ammonia and part of the water therein, passing the resulting heated mixture from said decomposer to a separator and expelling the resulting decomposer off gas stream containing said vaporized excess ammonia and part of the water from the residual urea-containing liquid phase of said major stream (2) in said separator, and contacting said resulting minor stream (3) directly with said decomposer off gas and with fresh carbon dioxide in a heat exchanger in indirect heat exchange with a relatively colder fluid, whereby carbon dioxide contained in said decomposer off gas and fresh carbon dioxide react with ammonia to form ammonium carbamate and a product containing the same, water, urea and ammonia is obtained, and heat of formation of said ammonium carbamate is transferred to said relatively colder fluid.

6. The process of claim 5, wherein said product so formed from said decomposer off gas, from said resulting stream (3) and from said fresh carbon dioxide, is recycled to said reactor.

7. The process for synthesizing urea, which comprises the sequence of steps consisting essentially of reacting ammonia and carbon dioxide in a reactor at elevated urea synthesis pressure to form an aqueous urea solution (1) containing ammonium carbamate, ammonia and water, splitting said aqueous solution (1) into a major stream (2) thereof and a minor stream (3) thereof, reducing the pressure of minor stream (3) to from about 60 to about 700 pounds per square inch, whereby excess ammonia gas is removed therefrom to form a residual minor stream (3), reducing the pressure of major stream (2) to from about 60 to about 700 pounds per square inch, heating said major stream (2) in an ammonium carbamate decomposer at a temperature above the decomposition temperature of ammonium carbamate to decompose a substantial portion of the ammonium carbamate therein to ammonia and carbon dioxide and vaporize part of the excess ammonia and part of the water therein passing the resulting heated mixture from said decomposer to a separator and expelling the resulting decomposer off gas stream containing said vaporized excess ammonia and part of the water from the residual urea-containing liquid phase of said major stream (2) in said separator, and contacting said residual minor stream (3) directly with said decomposer off gas and with fresh carbon dioxide in a heat exchanger in indirect heat exchange with a relatively colder fluid, whereby carbon dioxide contained in said decomposer off gas and fresh carbon dioxide react with ammonia to form ammonium carbamate and a product containing the same, water, urea and ammonia is obtained, and heat of formation of said ammonium carbamate is transferred to said relatively colder fluid.

8. The process of claim 7, wherein said product so formed from said decomposer off gas, from said residual minor stream (3) and from said fresh carbon dioxide, is recycled to said reactor.

9. The process for synthesizing urea, which comprises the sequence of steps consisting essentially of reacting ammonia and carbon dioxide in a reactor at elevated urea synthesis pressure to form an aqueous urea solution (1) containing ammonium carbamate, ammonia and water, splitting said aqueous solution (1) into a major stream (2) thereof and a minor stream (3) thereof, reducing the pressure of major stream (2) to from about 60 to 700 pounds per square inch, whereby excess ammonia gas is removed therefrom, to form a residual major stream (2), heating said residual major stream (2) in an ammonium carbamate decomposer at a temperature above the decomposition temperature of ammonium carbamate to decompose a substantial portion of the ammonium carbamate therein to ammonia and carbon dioxide, and vaporize part of the excess ammonia and part of the water therein passing the resulting heated mixture from said decomposer to a separator and expelling the resulting decomposer off gas stream containing said vaporized excess ammonia and part of the water from the residual urea-containing liquid phase of said major stream (2) in said separator, reducing the pressure of minor stream (3) to from about 60 to about 700 pounds per square inch, whereby excess ammonia gas is removed therefrom to form a residual minor stream (3) and contacting said minor stream (3) directly with said residual decomposer off gas and with fresh carbon dioxide in a heat exchanger in indirect heat exchange with a relatively colder fluid, whereby carbon dioxide contained in said decomposer off gas and fresh carbon dioxide react with ammonia to form ammonium carbamate and a product containing the same, water, urea and ammonia is obtained, and heat of formation of said ammonium carbamate is transferred to said relatively colder fluid.

10. The process of claim 9, wherein said product so formed from said decomposer off gas, from said minor stream (3) and from said fresh carbon dioxide, is recycled to said reactor.

* * * * *